United States Patent [19]

Hogen Esch

[11] 4,224,278

[45] Sep. 23, 1980

[54] APPARATUS FOR PERFORMING TESTS AND MEASUREMENTS ON LIQUID SAMPLES

[75] Inventor: Johannes H. L. Hogen Esch, Aalten, Netherlands

[73] Assignee: Vitatron Scientific B.V., Dieren, Netherlands

[21] Appl. No.: 895,389

[22] Filed: Apr. 11, 1978

[30] Foreign Application Priority Data

Apr. 22, 1977 [NL] Netherlands ............................ 7704460

[51] Int. Cl.² ............................ G01N 1/14; G01N 1/18
[52] U.S. Cl. ...................... 422/65; 141/130; 422/63
[58] Field of Search ............... 422/63, 65, 66, 100; 141/130

[56] References Cited

U.S. PATENT DOCUMENTS

| | | | |
|---|---|---|---|
| 3,430,415 | 3/1969 | Phillips | 53/123 |
| 3,544,272 | 12/1970 | Vaills | 422/65 |
| 3,568,735 | 3/1971 | Lancaster | 422/100 |
| 3,576,605 | 4/1971 | Drake et al. | 422/100 |
| 3,687,632 | 8/1972 | Natelson | 422/100 |
| 3,708,264 | 1/1973 | Jottier | 422/65 |
| 3,832,135 | 8/1974 | Drozdowski et al. | 422/65 |
| 3,852,035 | 12/1974 | Wood | 23/259 |
| 4,000,976 | 1/1977 | Kramer et al. | 422/65 |

FOREIGN PATENT DOCUMENTS

2260104 7/1975 France .
2237539 8/1975 France .

Primary Examiner—R. E. Serwin
Attorney, Agent, or Firm—Lane, Aitken & Ziems

[57] ABSTRACT

An apparatus for performing tests and measurements on liquid samples comprises three identical juxtaposed stationary trays each provided with a plurality of receptacles for the samples to be examined. The receptacles are integrally molded in the trays. The receptacles of the first tray serve as storage vessels for the samples, and the receptacles of the two other trays serve as processing vessels. Three stations arranged above the trays and displaceable with respect to the same in a horizontal plane serve for transferring the samples from the first tray to the second and the third tray, for adding reagents and for discharging the reaction products from the receptacles of the second and the third tray. Each of the stations comprises a carriage displaceable over the trays in an X-direction and a hollow needle for injecting and removing liquids supported by the carriage and displaceable with respect to the same in an Y-direction perpendicular to the X-direction. The carriages and the needles are driven by associated belts, each adapted to be displaced by an associated drum driven by a D.C. motor. The arrangement of the belts and the dimensions of the drums are such that the movement of a needle in one of the said directions does not involve a movement in the other direction, and that each carriage and each needle may be displaced through its entire range by one revolution of the associated drum.

17 Claims, 11 Drawing Figures fig.1 fig.2 fig.3 fig.4 fig.5 fig.6 fig.7 fig.8a fig.8b fig.9 ated the same into an empty receptacle on tray 2, optionally after a buffer liquid has been added to the serum. Similarly the carriage 7 with the needle 10 transfers a quantity of a starting reagent into the receptacle on tray 2. After the reaction has taken place the reaction mixture is removed from the receptacle on tray 2 by the needle 11 supported by carriage 8. For this purpose the needle 11 is hollow and is connected to a suction pipe, not shown. The receptacle on tray 2 is now empty again and can be used for another measurement. The reaction mixture removed by needle 11 can be led to a measuring apparatus, not shown.

APPARATUS FOR PERFORMING TESTS AND MEASUREMENTS ON LIQUID SAMPLES

BACKGROUND OF THE INVENTION

The invention relates to an apparatus for performing tests and measurements on various liquid samples, in particular sera.

A known apparatus of this kind comprises a first chain conveyor containing a series of receptacles. Indefinite quantities of the samples to be tested are each introduced into one of these receptacles. The receptacles are led by the conveyor through a first station in which definite quantity of each sample is transferred to a second conveyor also provided with a series of receptacles. Usually, a buffer reagent is added to each sample during the transfer. The second conveyor may also be a chain conveyor, or it may be a rotatable disc. The receptacles of the second conveyor are led through a second station in which a starting reagent is added to each sample, after which the receptacles are led through a third station, in which the reaction mixture in each receptacle is either removed by suction to be measure, or directly measured in its receptacle, according to the construction of the receptacles.

The known apparatus has the disadvantage that the samples may not be introduced into the first conveyor in an arbitrary order. In fact, the samples to be subjected to a same measurement must be placed one behind the other in the first conveyor. In addition, the known apparatus takes up much space.

BRIEF SUMMARY OF THE INVENTION

It is an object of the invention to provide an apparatus of the above-mentioned kind, into which the samples may be introduced in any desired order.

It is a further object of the invention to provide an apparatus of the above-mentioned kind which may accommodate a large number of samples per surface unit.

For this purpose, the apparatus according to the invention is characterized by three identical juxtaposed trays each provided with a plurality of receptacles, the receptacles of the first tray serving as storage vessels for the samples, and the receptacles of the second and the third tray serving as processing vessels, and by three stations arranged above the trays and displaceable with respect to the same in a horizontal plane, the said stations serving for transferring the samples from the receptacles of the first tray to those of the second or the third tray, for adding reagents, and for discharging the reaction products, respectively.

In the apparatus according to the invention, the samples on the first tray may be reached by the first station in any desired order, so that the samples need not be arranged in the first tray in a prescribed order. Also, the apparatus only takes up a relatively small space.

In a preferred embodiment of the invention, each of the said stations comprises a carriage displaceable over the three trays in an X-direction, and a hollow needle for injecting or removing a liquid, supported by the carriage and displaceable with respect to the same in an Y-direction perpendicular to the X-direction. Thus, an accurate positioning of the needles with respect to the receptacles may be obtained in a simple manner. The needles may be self-stirring.

Preferably, the displacement of each carriage in the X-direction and of each needle in the Y-direction is brought about by an associated belt, the driving arrangement for the needles being carried out in such manner that the displacement of a needle in one of the two directions does not involve a displacement in the other direction.

The belt for displacing the carriages and the drums may be driven by associated identical drums, each coupled with an associated D.C. motor through a speed reducing transmission. This allows for an economical series manufacture of the drums. The driving arrangements for the carriages and the needles may be constructed in such manner that a displacement of a carriage through its entire range in the X-direction, or of a needle through its entire range in the Y-direction requires only one revolution of the associated drum.

DETAILED DESCRIPTION

In the following description it has been presumed that the apparatus is used for testing or measuring sera, i.e. blood samples of various patients that are to be subject to different measurements. However, it will be clear that the apparatus according to the invention can also be used for other tests and measurements on any liquid samples that are to be examined in a laboratory.

Figure 1:
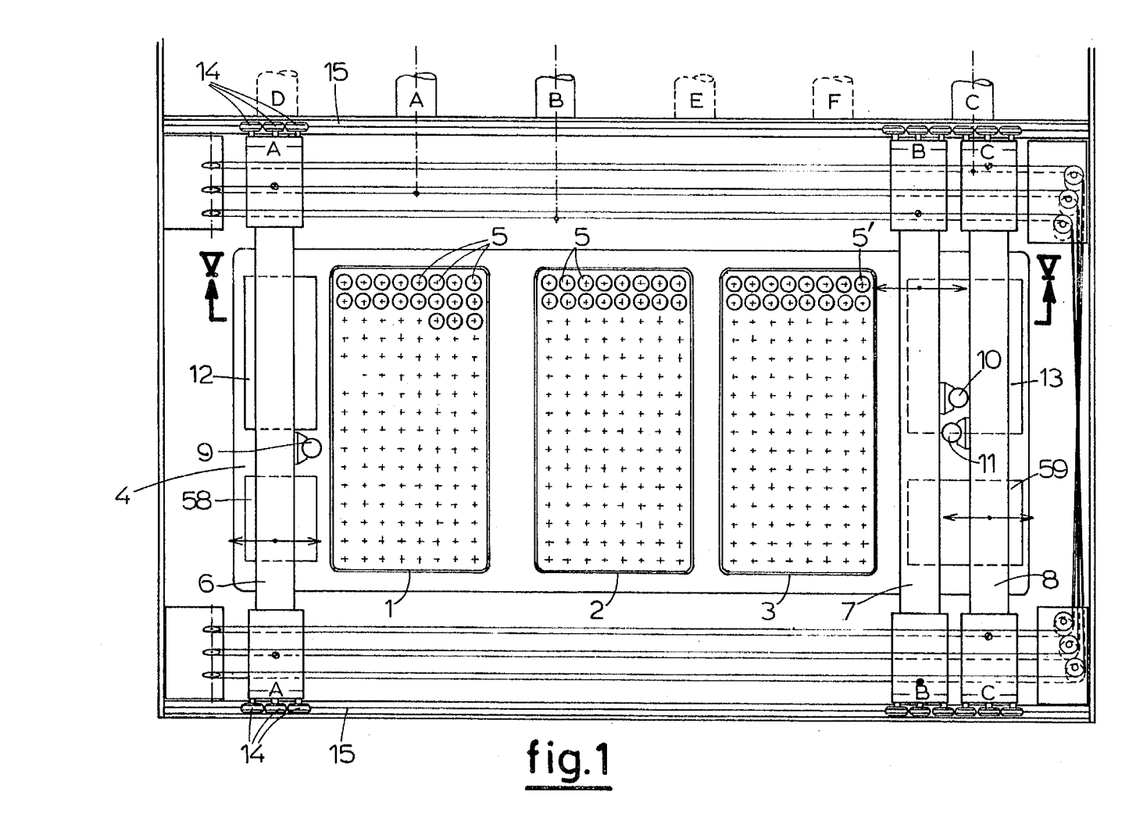
FIG. 1 shows a top view of an apparatus according to the invention, including the driving arrangement for the carriages.
Figure 2:
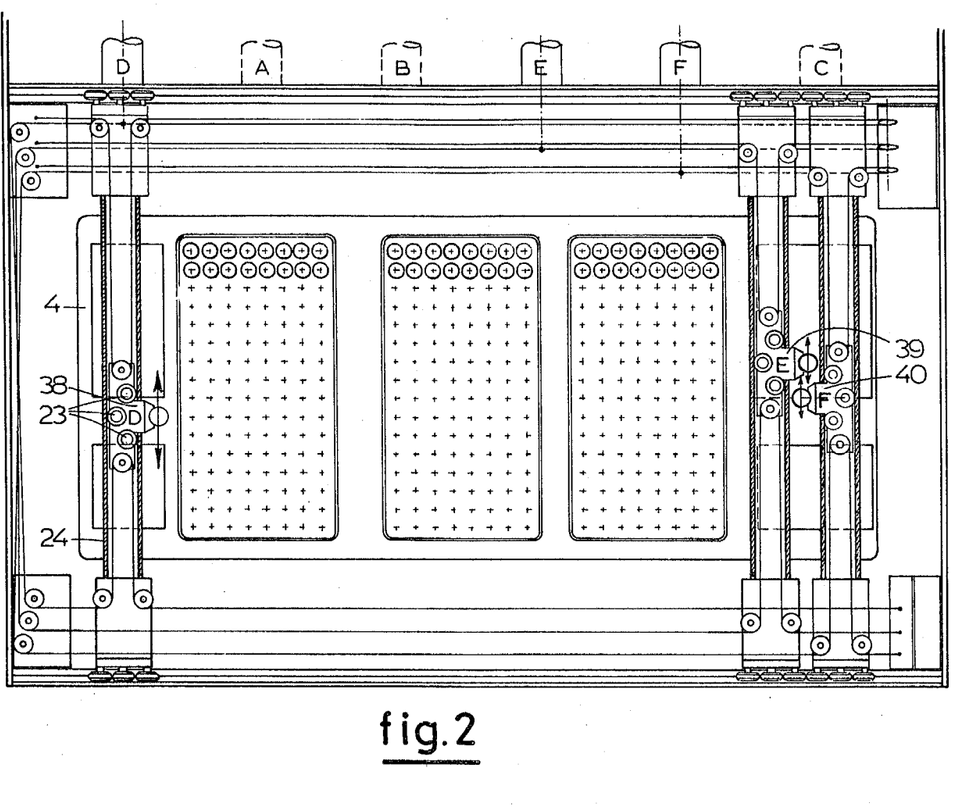
FIG. 2 shows a similar view of the apparatus according to FIG. 1, including the driving arrangements for the needles.

The apparatus shown in FIGS. 1 and 2 comprises three stationary trays 1, 2 and 3 mounted in a table 4, which may be moved up and down. Each tray comprises one hundred and twenty-eight receptacles 5 which are integrally moulded in the tray. The receptacles 5 of tray 1 serve as storage vessels for the sera, while the receptacles 5 of trays 2 and 3 serve as processing vessels.

Three carriages 6, 7 and 8, supporting needles 9, 10 and 11, respectively, are arranged above the trays. The carriages are movable over the trays in an X-direction and the needles are movable with respect to the carriages in an Y-direction perpendicular to the X-direction, so that any receptacle may be reached by needles. For the sake of clarity FIG. 1 only shows the driving arrangement for the carriages and FIG. 2 only shows the driving arrangement for the needles. The driving arrangements will be further explained hereinafter.

The carriage 6 with the needle 9 removes a definite quality of a serum from a receptacle on tray 1 and transfers this serum to one of the receptacles of tray 2 or 3. The serum is injected into the latter receptacle together with a buffer reagent. The needle 9 performs a stirring movement during the injection and during its removal from the liquid, so that no liquid drops remain attached to the needle when it leaves a receptacle. In addition, the serum is intimately mixed with the buffer reagent. After the transfer of the serum carriage 6 returns to its starting position in which a cleaning device 12 is arranged. The needle 9 is rinsed in this cleaning device, after which a serum may be injected in a next receptacle 5. If desired, a separate needle may be used for the buffer reagent.

After carriage 6 has injected a serum into a receptacle, carriage 7 may add after a predetermined time a starting reagent. After a predetermined reaction time needle 11 of carriage 8 removes the mixture from the receptacle to be photometrically examined by means of flow cell or the like.

The needles 10 and 11 of the carriages 7 and 8 also perform a stirring movement during an injection and during the removal from the liquid in order to prevent liquid drops from being attached. At the same time the starting reagent is intimately mixed with the serum by needle 10. A cleaning device 13 has been provided for the needles 10 and 11, in which they are rinsed after each operation.

Figure 5:
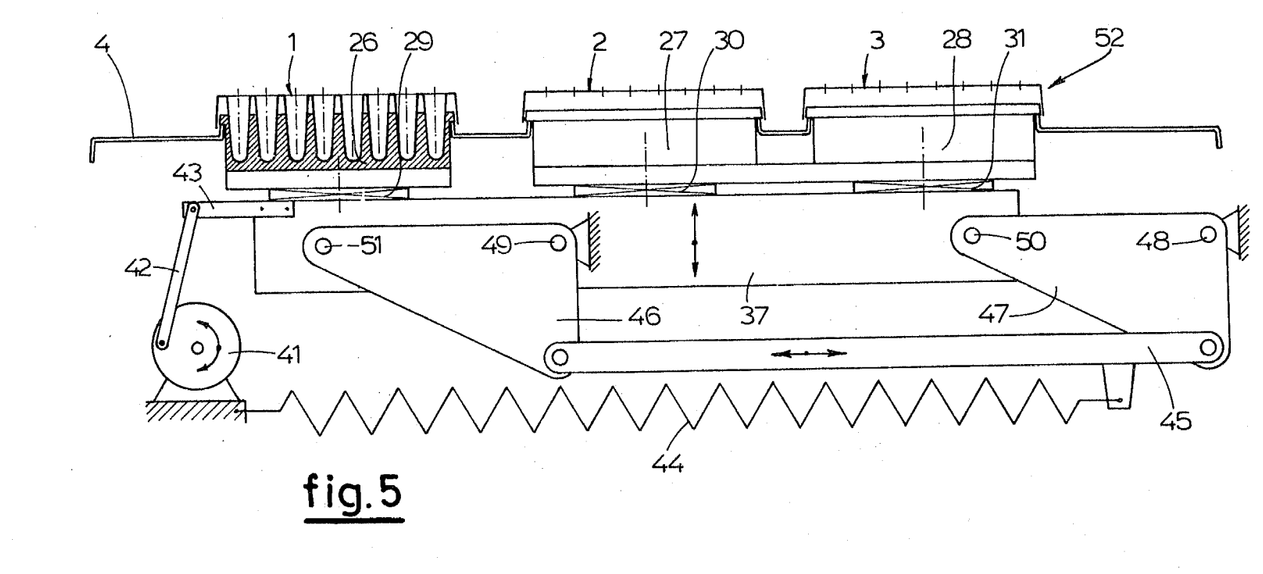
FIG. 5 shows a cross section along the line V—V in FIG. 1.

FIG. 5 shows that the trays 1, 2 and 3 are placed in carriers 26, 27 and 28, respectively. The carriers consist of aluminum blocks which are heated to a desired temperature and maintained at the same by means of Peltier elements 29, 30 and 31, which are arranged on a platform 37. The carriers 26, 27 and 28 are constructed in such manner that a good contact is obtained with the receptacles, so that the temperature of the liquid is substantially equal to the temperature of the block. The carriers 26, 27 and 28, the Peltier elements 29, 30 and 31, the platform 37 and the table 4 constitute an assembly 52 which may be moved up and down. By the upward movement of the assembly 52 the needles may be introduced into the receptacles 5 or into the cleaning devices 12 and 13 for the removal or injection of a serum, or for rinsing, respectively. The upward movement is provided by a motor which drives a pin 43, attached to the platform 37 by means of a disc 41 and a rod 42. The motor needs only produce a slight force, because the weight of the assembly 52 is compensated for a major part by a spring 44 exerting a force on the assembly 52 by means of a rod 45 and a pair of tumblers 46 and 47. Because the fixed joinings 48 and 49 are in one horizontal line with the hinges 50 and 51 coupling the tumblers 46 and 47 with the platform 37, and because the total displacement is small, the movement of the assembly 52 will be a vertical translation.

The carriages are simultaneously moved to the left or to the right, so that they do not interfere with each other. For instance, carriage 6 may be in its starting position for cleaning purposes, while carriage 7 adds a starting reagent to a receptacle and carriage 8 removes a sample for measuring purposes.

The first receptacle to be filled on tray 3 is indicated by 5'. After that the receptacles are successively filled in the Y-direction. When all receptacles 5 of tray 3 have been filled, tray 2 is used for further operation. The "distance" between carriages 6 and 8 may be, for instance, at most one hundred and twenty receptacles. In this case it is certain that carriage 8 operates on tray 2, when carriage 6 has filled all the receptacles of tray 2. The operation on tray 3 has been finished at that time, so that it may be replaced by a new tray, on which carriage 6 may continue its operation, when all receptacles of tray 2 have been filled.

The apparatus performs a series of measurements of a same kind directly after each other. For instance, if a measurement A has to be performed on fifty sera of tray 1, the carriage 6 transfers these sera to fifty subsequent receptacles of tray 2 or 3. Since the needle 9 of carriage 6 may reach the receptacles of tray 1 in any desired order, the sera need not be placed in the receptacles of tray 1 in any prescribed order.

After the first series of measurements has been finished, a next series may be started, for instance thirty measurements B. For this purpose the sera are transferred to the next thirty receptacles of tray 2 or 3.

The duration of a cycle, i.e. the time required for a complete treatment, such as rinsing, sucking up and injecting for carriage 6, may be 15, 20, 25 or 30 seconds, so that for a maximum distance of one hundred and twenty receptacles between carriages 6 and 8 the following incubation times are obtained between the injection of a serum together with the buffer reagent and the measurement:

15 sec. up to 30 min., max. 240 measurements/h
20 sec. up to 40 min., max. 180 measurements/h
25 sec. up to 50 min., max. 144 measurements/h
30 sec. up to 60 min., max. 120 measurements/h The moment at which the starting reagent is added may be selected within the above limits.

The carriages 6, 7 and 8 are provided at each end with three wheels 14 running in a U-profile 15, so that the carriages may also move in the X-direction. The carriages and the needles are each driven by a D.C. motor by means of a belt. Motors A, B and C serve for the displacement of carriages 6, 7 and 8 in the X-direction, while motors D, E and F serve for the displacement of the needles in the Y-direction. As appears from FIG. 2, the needles are attached to needle carriers 38, 39 and 40, each running with three wheels 23 in a U-profile 24.

Figure 3:
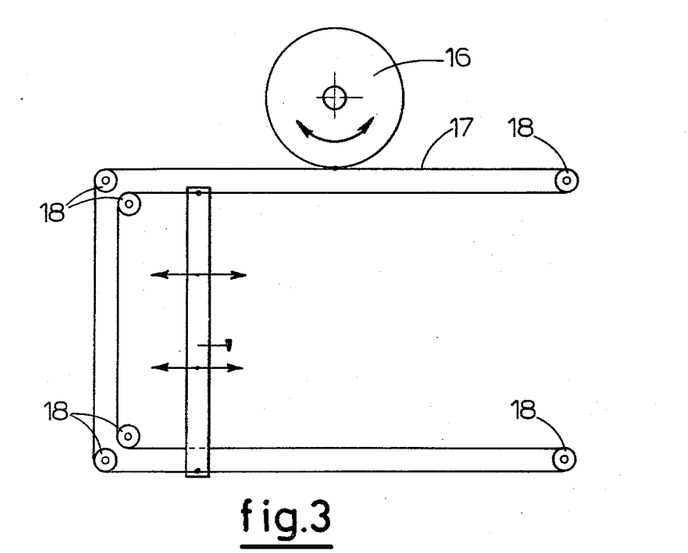
FIG. 3 shows a schematic representation of the driving arrangement for the carriages.

The driving arrangement for the X-direction is schematically shown in FIG. 3. A drum 16 is driven by the motor with a speed reduction of 1:36. The drum 16 displaces a belt 17 guided by rollers 18 and attached to a carriage with both ends. The circumference of drum 16 has been selected in such manner that a complete displacement in the X-direction requires one revolution of the drum.

Figure 4:
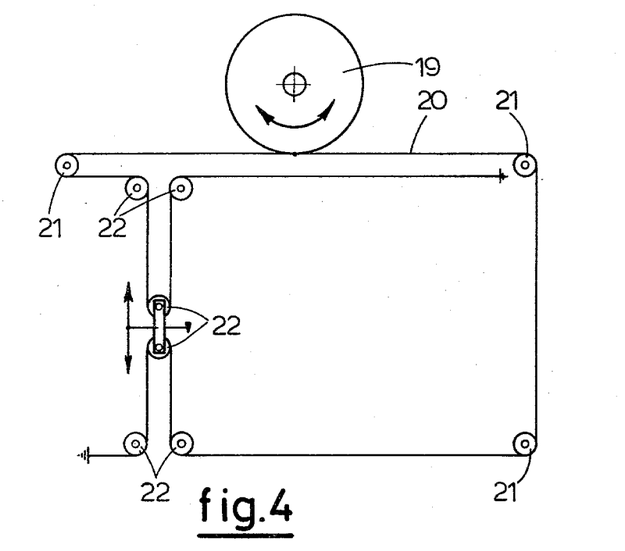
FIG. 4 shows a schematic representation of the driving arrangement for the needles.

The driving arrangement for the Y-direction is schematically shown in FIG. 4. A drum 19 displaces a belt 20 guided by rollers 21 and 22, of which the rollers 22 are arranged on the carriage. The total path in the Y-direction is half the total path in the X-direction. Due to the arrangement of the rollers as shown the length of the belt to be displaced for the Y-direction is twice the length to be displaced for the X-direction. This makes it possible to use identical drums for both movements, so that a complete displacement in the Y-direction also requires only one revolution of the drum.

The motors for the movement in both directions are fixedly attached to the apparatus. The driving arrangement as shown ensures that a movement in the X-direction does not involve the movement in the Y-direction and vice versa.

Figure 6:
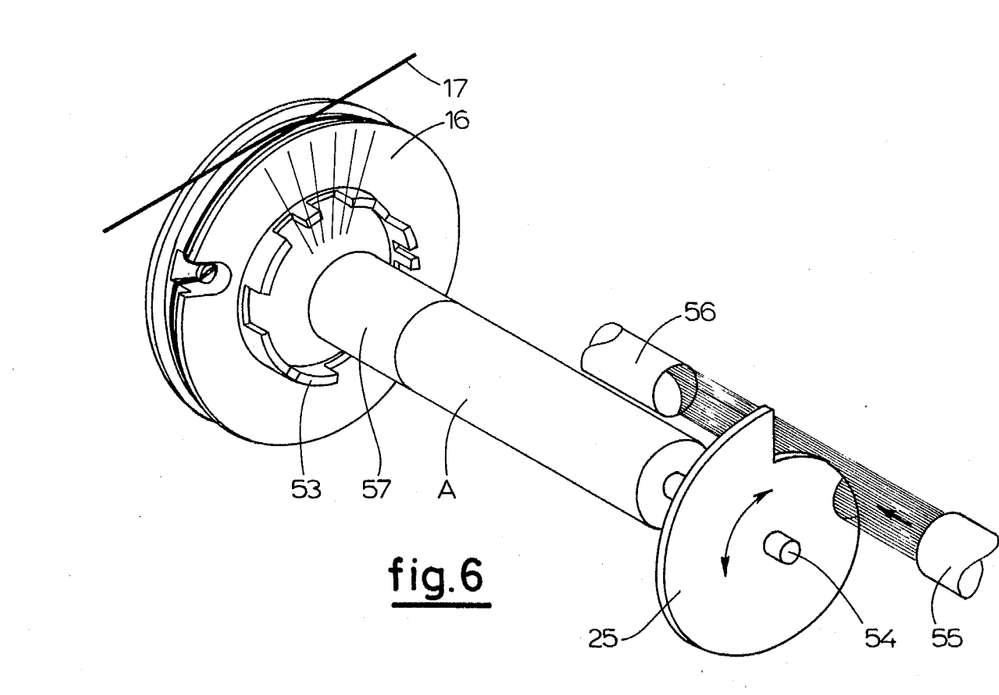
FIG. 6 shows a perspective view of a driving motor, including the various parts of the position control.
Figure 7:
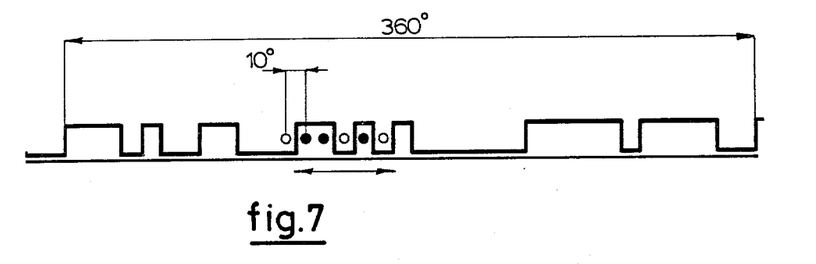
FIG. 7 shows a developed view of an axially extending edge of a drum provided with a binary series code.

The needles are brought above the desired receptacles by means of positioners, each comprising a digital and an analogue portion. The digital positioning is performed stepwise by means of a binary series code provided in an axially extending edge 53 of the drum 16, as shown in FIG. 6. FIG. 7 shows a development of the edge 53. A complete revolution of drum 16 corresponds with 36 steps. A step is the distance of a central position between two adjacent receptacles 5 to a central position between the two adjacent receptacles 5. Due to the speed reduction of 36:1 in the transmission 57 one step corresponds exactly with one revolution of the motor shaft 54. The binary series code is converted into electric signals by six light sources, cooperating with six photocells (not shown in FIG. 6). The binary series code is converted into an ordinary binary code, counting from 0 to 35 by a programmable permanent memory, so that the required position of a needle may be determined in a simple manner.

Figure 8A:
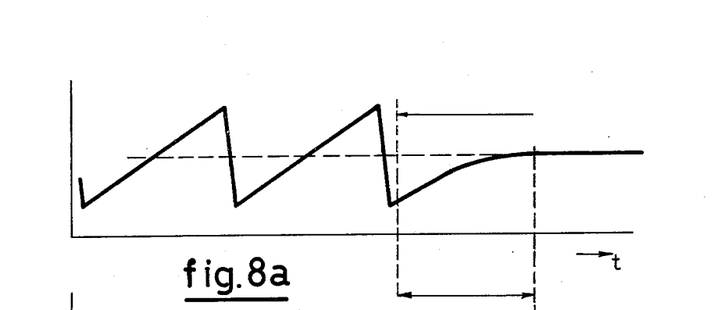
FIG. 8a shows a diagram of the voltage produced by the photocell.
Figure 8B:
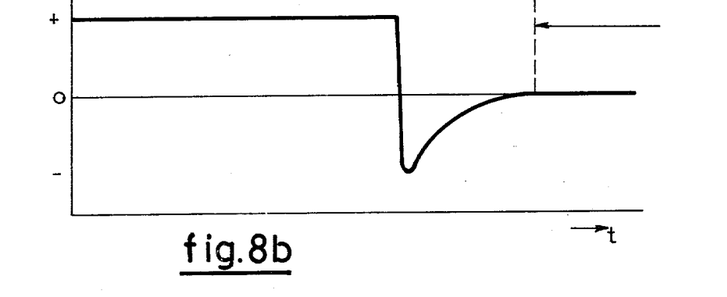
FIG. 8b shows a diagram of the associated motor voltage.

As soon as the right code has been reached, the positioning is switched over to the analogue portion. The required voltage is generated by a spiral disc 25 arranged on the motor shaft 54 and placed with its spiral edge in the path of a tight beam thrown by a light source 55 on a photocell 56. Thus, during each revolution of the motor shaft 54 the exposure of the photocell 56 increases from a minimum to a maximum value, so that the photocell 56 produces a sawtooth voltage as shown in FIG. 8a. By comparing this voltage with a reference voltage, of which the value lies between the minimum and the maximum of the sawtooth voltage in a PD control unit, the accurate position of the motor shaft 54 is obtained. Due to the differentiating action of the control unit the shaft is strongly braked after the switch-over to the analogue portion, so that the needle does not overshoot but immediately reaches the correct position above the receptacle 5. The voltage delivered by the PD control unit to the motor is shown in FIG. 8b.

The positioning might also be obtained exclusively with the analogue portion by counting the number of cycles of the sawtooth voltage. However, the combination of a digital and an analogue operation has the advantage that the accuracy and the reproduceability of each discrete step is high and independent of the number of steps.

Figure 9:
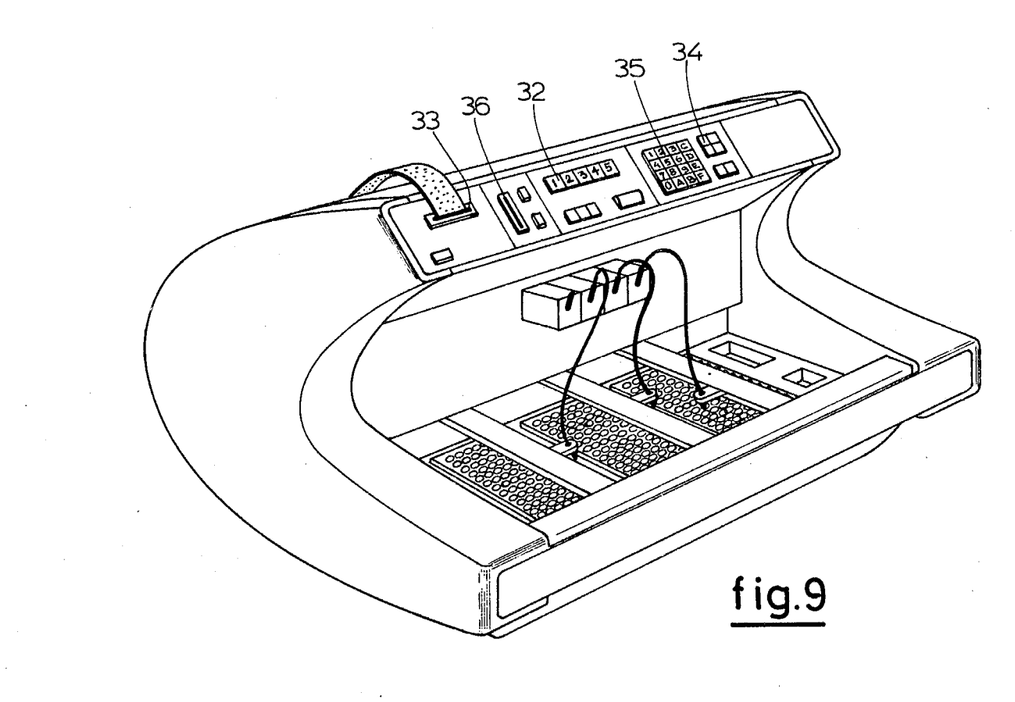
FIG. 9 shows an overall view of the apparatus as shown in the previous Figures.

The apparatus is provided with a photometer for performing the measurements. The results may be indicated by a digital display 32 and/or a printer 33 (FIG. 9).

Furthermore, the apparatus is provided with an operating key-board 34, and entering key-board 35 and a reading and writing device 36 for magnetic cards or tapes. By means of these provisions the apparatus may receive information required for the operation to be performed. The circuits for processing this information and for controlling the carriages, the needles and the table may be carried out in the usual manner.

Apart from the above described series of operations performed in the apparatus it is also possible to perform a part of these operations outside the apparatus. For instance, tray 2 and 3 may be filled and prepared by means of reagents outside the apparatus and introduced in the apparatus after that, so that the apparatus only performs the measurement.

The apparatus may be tested by introducing a checking serum into a receptacle of tray 2 or 3 by means of a pipette. After that the number of the receptacle is inserted by hand, together with information about the desired operations. Carriage 6 removes the required quantity of the serum and transfers it to another receptacle in which the same operations are performed as for a normal serum.

A serum blank, i.e. a serum with a buffer reagent and two portions of distilled water, may be obtained by removing a serum by means of the needle 9 from a receptacle of tray 1 and injecting it together with a buffer reagent into another receptacle, and by adding to the latter receptacle distilled water from a tank 59 instead of a starting reagent.

I claim:

1. Apparatus for performing tests and measurements on various liquid samples, in particular sera, comprising three identical juxtaposed trays each provided with a plurality of receptacles for the samples to be examined, the receptacles of a first one of the said trays serving as storage vessels for the samples, and the receptacles of a second and a third one of the said trays serving as processing vessels for the samples, and further comprising three stations arranged above the said trays and means for displacing said stations with respect to said trays in all directions in a horizontal plane, the said stations serving for transferring the samples from said first tray to said second and said third tray, for adding reagents, and for discharging reaction products from the receptacles of said second and said third tray.

2. Apparatus as claimed in claim 1, wherein the said receptacles consist of recesses integrally molded in the said trays.

3. Apparatus as claimed in claim 1, wherein each of the said stations comprises a carriage displaceable over the said trays in an X-direction, and a hollow needle for injection or removing a liquid supported by the associated carriage and displaceable with respect to the same in an Y-direction perpendicular to said X-direction.

4. Apparatus as claimed in claim 3, further comprising means for subjecting each of the said needles to a stirring movement during an injection, and during its removal from a sample.

5. Apparatus as claimed in claim 3, further comprising a first plurality of belts each adapted to drive one of the said carriages in said X-direction, and a second plurality of belts each adapted to drive one of the said needles in said Y-direction, the belt of said second plurality being arranged in such manner that a movement of one of the said needles in one of the said directions does not involve a movement in the other one of the said directions.

6. Apparatus as claimed in claim 5, further comprising a plurality of identical drums each adapted to displace one of the said belts, a plurality of D.C. motors each associated with one of said drums, and a plurality of speed reducing transmissions each coupling one of the said motors with the associated drum, the circumference of the said drums being selected in such manner that a displacement of one of the said carriages through its entire range in the X-direction, or a displacement of one of the said through its entire range in the Y-direction requires only one revolution of the associated drum.

7. Apparatus as claimed in claim 6, further comprising a plurality of positioners, each associated with one of the said drums and each comprising a discrete positioning portion and a linear positioning portion.

8. Apparatus as claimed in claim 7, wherein the discrete positioning portion of each of the said positioners includes an axially extending edge of the associated drum provided with a plurality of openings arranged according to a binary code, a plurality of light sources cooperating with the said openings, and a plurality of photocells each cooperating with one of the said light sources.

9. Apparatus as claimed in claim 7, wherein the linear positioning portion of each of the said positioners comprises a spiral disc directly coupled with the associated motor, a light source projecting a light beam on the edge of said spiral disc, a photocell cooperating with said light source to produce a sawtooth voltage during each step of the associated discrete positioning portion, and a comparator comparing said sawtooth voltage with a fixed reference voltage having a value between the maximum and minimum values of said sawtooth voltage.

10. Apparatus as claimed in claim 9, wherein each of the comparators associated with said needles comprises means adapted to substitute a sinusoidal voltage for said fixed reference voltage, so as to impart a stirring movement to the associated needle.

11. Apparatus as claimed in claim 1, further comprising a plurality of carriers each receiving one of said trays, and a plurality of Peltier elements each maintaining one of the said carriers at a predetermined temperature.

12. Apparatus as claimed in claim 11, further comprising a common platform supporting the said carriers, a plurality of cleaning devices for the needles supported by said platform, a plurality of water tanks associated with the said cleaning devices and supported by said platform, and means for imparting an upward movement to said platform in order to immerse the said needles in the said receptacles and in the said cleaning devices.

13. Apparatus as claimed in claim 3, further comprising two fixed U-profiles extending in said X-direction, wherein each of the said carriages is provided with three wheels at one of its ends running in one of the said U-profiles, and with three wheels at its other end running in the other one of the said U-profiles.

14. Apparatus as claimed in claim 3, further comprising three U-profiles each attached to one of the said carriages and each extending in said Y-direction, and three needle holders each associated with one of the said carriages and supporting the associated needle, each of the said needle holders being provided with three wheels running in the U-profile attached to the associated carrier.

15. Apparatus as claimed in claim 1, further comprising a writing and reading device adapted to cooperate with a magnetic information carrier, a printer, a digital display, and operating key-board, and a key-board for entering the required information.

16. Apparatus as claimed in claim 1, further comprising a flow cell photometer for measuring certain properties of the samples.

17. Apparatus as claimed in claim 1, further comprising means on said first station for adding a buffer reagent to each sample during its transfer to the second or the third tray.

* * * * *